US00PP15381P2

(12) United States Plant Patent

Noordhuis

(10) Patent No.: US PP15,381 P2

(45) Date of Patent: Nov. 30, 2004

(54) *AGASTACHE* PLANT NAMED 'PINK PERFUME'

(50) Latin Name: *Agastache rugosa×Agastache pallidiflora*
Varietal Denomination: Pink Perfume

(75) Inventor: Bart Noordhuis, Boyl (NL)

(73) Assignee: Inspiration Plant CV, Lisse (NL)

( * ) Notice: Subject to any disclaimer, the term of this patent is extended or adjusted under 35 U.S.C. 154(b) by 0 days.

(21) Appl. No.: 10/624,104

(22) Filed: Jul. 21, 2003

(51) Int. Cl.[7] ..... A01H 5/00

(52) U.S. Cl. ..... Plt./263

(58) Field of Search ..... Plt./263

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Agastache* plant named 'Pink Perfume', characterized by its upright, mounded and compact plant habit; freely flowering habit with numerous spikes per plant and numerous flowers per spike; and red purple-colored flowers.

1 Drawing Sheet

Botanical classification/cultivar designation: *Agastache rugosa×Agastache pallidiflora* cultivar Pink Perfume.

BACKGROUND OF THE INVENTION

The present Invention relates to a new and distinct cultivar of *Agastache* plant, botanically known as *Agastache rugosa×Agastache pallidiflora*, and hereinafter referred to by the name 'Pink Perfume'.

The new *Agastache* is a product of a planned breeding program conducted by the Inventor in Boyl, The Netherlands. The new *Agastache* was discovered and selected by the Inventor in a seed bed of sown *Agastache* seed from various cross-pollinations of unnamed *Agastache rugosa* seedling selections, not patented, with unnamed *Agastache pallidiflora* seedling selections, not patented, in a controlled environment in Boyl, The Netherlands in 1998. The new *Agastache* was selected as an individual seedling within the progeny of these various cross-pollinations on the basis of its compact plant habit and red purple-colored flowers.

Asexual reproduction of the new cultivar by vegetative cuttings taken at Boyl, The Netherlands, has shown that the unique features of this new *Agastache* are stable and reproduced true to type in successive generations.

SUMMARY OF THE INVENTION

Plants of the cultivar Pink Perfume have not been observed under all possible environmental conditions. The phenotype may vary somewhat with variations in environment such as temperature and light intensity without, however, any variance in genotype.

The following traits have been repeatedly observed and are determined to be the unique characteristics of 'Pink Perfume'. These characteristics in combination distinguish 'Pink Perfume' as a new and distinct *Agastache* cultivar:

1. Upright, mounded and compact plant habit.
2. Freely flowering habit with numerous spikes per plant and numerous flowers per spike.
3. Red purple-colored flowers.

Plants of the new *Agastache* are most similar to plants of the parent selections. Compared to plants of the parent selections, plants of the new *Agastache* are more compact, have deeper red purple flower coloration, and flower for a longer period of time.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Agastache*.

The photograph at the top of the sheet comprises a side perspective view of a typical flowering plant of 'Pink Perfume' grown in an outdoor nursery.

The photograph at the bottom of the sheet is a close-up view of a typical flowering spike of 'Pink Perfume'.

DETAILED BOTANICAL DESCRIPTION

Plants shown in the aforementioned photographs and used in the following description were grown under conditions which closely approximate commercial production conditions during the spring and summer in an outdoor nursery in Boyl, The Netherlands. Plants in the photographs and those used for the description were about one year old and in a 17.5 cm. container when the photographs and description were taken. In the following description, color references are made to The Royal Horticultural Society Colour Chart, 1995 Edition, except where general terms of ordinary dictionary significance are used.

Botanical classification: *Agastache rugosa×Agastache pallidiflora* cultivar Pink Perfume.

Parentage:

*Female, or seed, parent.*—Unnamed *Agastache rugosa* seedling selection, not patented.

*Male, or pollen, parent.*—Unnamed *Agastache pallidiflora* seedling selection, not patented.

Propagation:

*Type.*—By vegetative cuttings.

*Time to initiate and develop roots.*—About 14 days during the spring under outdoor production conditions, about 15° C.

*Root description.*—Numerous; fine.

Plant description:

*Form.*—Perennial. Upright, mounded and compact plant habit; broad inverted triangle. Flowering stems arise from the roots; moderate branching from the stems, typically about six to eight lateral branches per plant; dense and bushy plant habit; moderate to vigorous growth habit. Freely flowering with numerous flowering spikes per plant and numerous flowers arranged in verticillasters on crowded spikes.

*Plant height.*—About 45 cm.

*Plant width.*—About 35 to 45 cm.

*Stem description.*—Diameter: About 3 mm. Internode length: About 6 to 15 cm. Strength: Strong. Texture: Smooth, glabrous. Color: 139A.

*Foliage description.*—Arrangement: Opposite, simple. Length: About 4 to 6.5 cm. Width: About 1.8 to 3 cm. Shape: Lanceolate to ovate. Apex: Acute. Base: Obtuse. Margin: Serrate. Texture, upper and lower surfaces: Smooth, glabrous. Venation pattern: Pinnate. Fragrance: When rubbed, strong peppermint scent. Color: Developing and fully expanded foliage, upper surface: 137A; venation, 137A. Developing and fully expanded foliage, lower surface: 138B; occasional red purple areas, close to 187B; venation similar to lamina. Petiole length: About 1 to 2.5 cm. Petiole diameter: About 1.5 to 2 mm. Petiole color: 139A.

Flower description:

*Flower arrangement and shape.*—Numerous single labiate flowers arranged in verticillasters on terminal spikes; flowers face mostly outwardly. Freely flowering, about 1,200 to 1,500 flowers and flower buds per plant.

*Natural flowering season.*—Continuous flowering from the late spring through fall in The Netherlands.

*Flower longevity on the plant.*—Individual flowers last about one week on the plant. Flowers not persistent.

*Fragrance.*—When rubbed, strong peppermint scent.

*Flower buds* (*about one day before opening*).—Length: About 0.5 mm. Diameter: About 2 mm. Shape: Obovate. Color: 36A.

*Flowers.*—Diameter: About 7 to 9 mm. Depth (height): About 5 mm.

*Petals.*—Arrangement: Labiate; corolla two lipped, upper lip erect with two lobes, lower lip with three lobes; lips fused at the base. Length: About 7 to 9 mm. Shape: Oblanceolate. Apex: Acute to obtuse. Margin: Entire. Texture, upper and lower surfaces: Smooth, glabrous. Color: When opening and fully opened, upper surface: 69B. When opening and fully opened, lower surface: 69B.

*Sepals.*—Arrangement: Five sepals fused into a tube. Calyx length: About 4 to 5 mm. Calyx width: About 2 mm. Apex: Acuminate. Margin: Entire. Texture, upper and lower surfaces: Smooth, glabrous. Color, upper and lower surfaces: 60C.

*Pedicels.*—Strength: Moderately strong. Length: About 1 to 2 mm. Diameter: Less than 1 mm. Aspect: About 40 to 50° from vertical. Color: 138C.

*Reproductive organs.*—Stamens: Quantity per flower: About four. Anther attachment: Dorsifixed. Anther length: About 0.7 to 1 mm. Anther color: 18C. Pollen amount: Sparse. Pollen color: Creamy white. Pistils: Quantity per flower: One. Pistil length: About 0.7 to 0.9 mm. Stigma shape: Three-parted; recurved. Stigma color: 185A. Style length: About 0.7 to 0.9 mm. Style color: 69B. Ovary color: 72C.

*Seed.*—Length: About 1 mm. Diameter: About 1 mm. Color: Black, close to 202A.

Disease/pest resistance: Plants of the new *Agastache* have not been noted to be resistant to pathogens and pests common to *Agastache*.

It is claimed:

1. A new and distinct cultivar of *Agastache* plant named 'Pink Perfume', as illustrated and described.

* * * * *

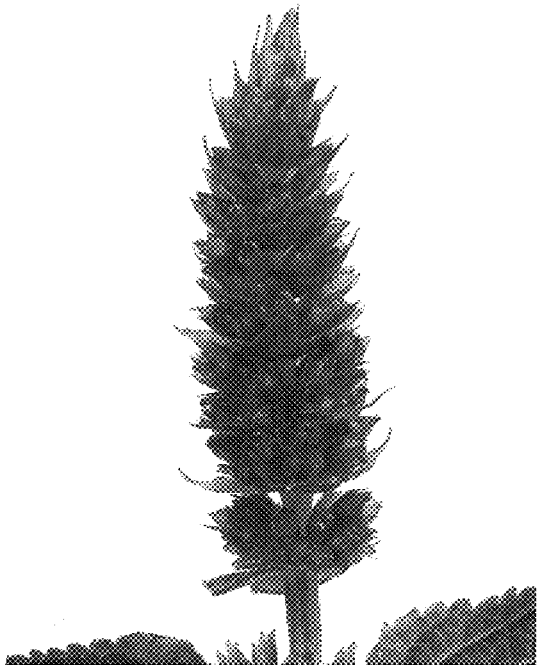
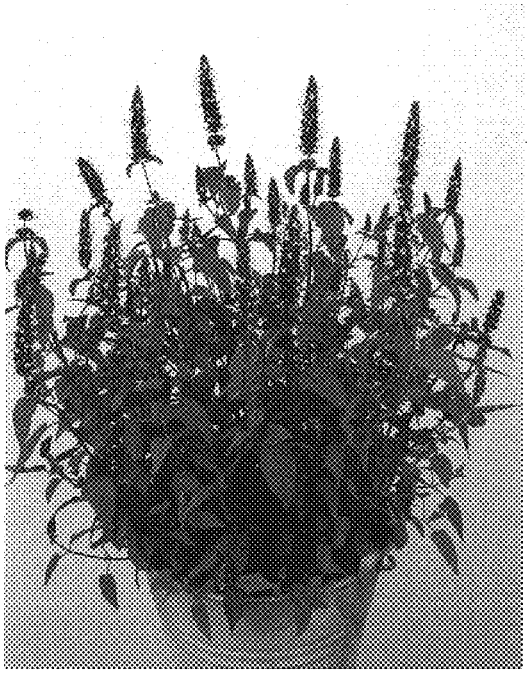
Pink Perfume